United States Patent
Negishi (10) Patent No.: US 7,828,726 B2
(45) Date of Patent: Nov. 9, 2010

(54) ENDOSCOPE LIGHT SOURCE UNIT

(75) Inventor: Kiyoshi Negishi, Saitama (JP)

(73) Assignee: Hoya Corporation, Tokyo (JP)

( * ) Notice: Subject to any disclaimer, the term of this patent is extended or adjusted under 35 U.S.C. 154(b) by 1031 days.

(21) Appl. No.: 11/559,106

(22) Filed: Nov. 13, 2006

(65) Prior Publication Data

US 2007/0112253 A1 May 17, 2007

(30) Foreign Application Priority Data

Nov. 15, 2005 (JP) .............................. P2005-330457

(51) Int. Cl.
*A61B 1/06* (2006.01)
(52) U.S. Cl. ........................ 600/178; 600/180; 600/181; 362/574
(58) Field of Classification Search .................. 600/178, 600/180, 181, 118; 348/68, 74; 362/574
See application file for complete search history.

(56) References Cited

U.S. PATENT DOCUMENTS

| | | | | |
|---|---|---|---|---|
| 2,063,222 A | * | 12/1936 | Beau | 356/70 |
| 3,848,985 A | * | 11/1974 | Bennett | 396/207 |
| 4,249,807 A | * | 2/1981 | Webster et al. | 396/548 |
| 4,322,129 A | * | 3/1982 | Takahashi et al. | 359/230 |
| 4,618,260 A | * | 10/1986 | Okubo | 356/331 |
| 4,901,144 A | * | 2/1990 | English et al. | 348/69 |
| 5,006,965 A | * | 4/1991 | Jones | 362/552 |
| 5,515,119 A | * | 5/1996 | Murdock et al. | 352/131 |
| 5,642,456 A | * | 6/1997 | Baker et al. | 385/140 |
| 5,896,224 A | * | 4/1999 | Kapitza | 359/389 |
| 5,971,919 A | * | 10/1999 | Davis | 600/180 |
| 6,724,418 B1 | * | 4/2004 | Takahashi | 348/65 |
| 7,018,331 B2 | * | 3/2006 | Chang et al. | 600/182 |
| 7,029,437 B2 | * | 4/2006 | Kobayashi | 600/180 |
| 2005/0159646 A1 | * | 7/2005 | Nordstrom et al. | 600/127 |
| 2007/0010712 A1 | | 1/2007 | Negishi | |
| 2007/0010713 A1 | | 1/2007 | Negishi | |
| 2007/0010714 A1 | | 1/2007 | Negishi | |

FOREIGN PATENT DOCUMENTS

JP 2003-305008 10/2003

OTHER PUBLICATIONS

English language Abstract of JP 2003-305008.

* cited by examiner

*Primary Examiner*—John P Leubecker
(74) *Attorney, Agent, or Firm*—Greenblum & Bernstein, P.L.C.

(57) ABSTRACT

An endoscope light source unit including a light source, for making illumination light incident on a light guide of an endoscope which is disconnectably connected to the endoscope light source unit, the endoscope light source unit includes an aperture device including aperture openings of different opening ratios which are selectively positioned between the incident end face of the light guide and the light source; a reading device for reading endoscope-type information from a memory provided in the endoscope; and a controller for selecting one aperture opening, an opening ratio of which corresponds to the endoscope-type information, for making the selected one aperture opening positioned between the incident end face of the light guide and the light source, and for allowing the light source to be turned ON. The controller prohibits the light source from being turned ON if the reading device cannot read the endoscope-type information.

10 Claims, 6 Drawing Sheets

ENDOSCOPE LIGHT SOURCE UNIT

BACKGROUND OF THE INVENTION

1. Field of the Invention

The present invention relates to an endoscope light source unit suitable for an endoscope or an electronic endoscope, etc.

2. Description of the Related Art

Recent electronic endoscope systems have provided therein a processor with a built-in light source unit for lighting, to which an electronic scope having an electronic camera mounted on the distal end thereof or a fiber scope for conducting observation only through optical members is connected for use. In particular, electronic scopes have been provided for use with a wide variety of thicknesses and functions suited to different locations of observation. Processors connectable with various types of electronic scopes and fiber scopes must also have light source units that are compatible with such various electronic scopes and fiber scopes. For this reason, conventional light source units have been constructed so as to supply necessary amounts of illumination light to electronic scopes that require a maximum light quantity.

Such light source units are configured such that illumination light emitted from a high-intensity lamp is condensed by a condenser lens and made incident on the incident end face of a scope light guide (typically an optical fiber bundle). Since the necessary quantity of illumination light varies in accordance with the type of electronic scope and with the observation location, the light source units are equipped with an aperture device for mechanically adjusting the amount of light. Among known aperture devices is one that includes a diaphragm which is composed of a partly-notched portion and an arm portion integrated with the partly-notched portion, having a size such that all the light from a light source lamp can be blocked, and a motor mechanically connected to an end of the arm portion. The motor is rotated to turn the diaphragm about the top of the arm portion, thereby changing the degree of illumination light blocked by the partly-notched portion to adjust the illumination quantity (see Japanese Patent Laid-Open Publication No. 2003-305008). Moreover, a light shielding plate may be provided with a plurality of aperture openings having different opening ratios or transmittances so as to form a rotary aperture plate which regulates the amount of light incident on the incident end face of a light guide by putting one of the aperture openings selectively between a light source unit and the incident end face of the scope light guide (i.e., into the illumination optical path).

Such a light source unit uses high-intensity lamps such as a metal halide lamp or a xenon lamp. The higher intensities the lamps have, the more heat components the illumination light contains. Consequently, depending on the type of scope, the light source unit may be excessively intense, and also may heat up the end of the scope due to the heat components of the illumination light unless the quantity of the light source unit is turned down (reduced). Some light source units adjust picture brightness without activating aperture devices but by adjusting the electronic shutter speed. In such a light source unit, pictures (images) of appropriate brightness can be obtained by increasing the electronic shutter speed, whereas an excessively high quantity of the illumination light can heat up the end of the light guides, i.e., the distal end of the scope.

SUMMARY OF THE INVENTION

The present invention has been achieved in view of the foregoing problems of the prior art. The present invention provides an endoscope light source unit which can prevent problems such as overheating of a scope from occurring even if a scope, whose information on the maximum amount of illumination light allowable into the scope from the endoscope light source, illumination-light quantity limit and other information is unknown, is connected to the endoscope light source unit.

According to an aspect of the present invention, An endoscope light source unit is provided, including a light source, for making illumination light from the light source incident on an incident end face of a light guide of an endoscope which is disconnectably connected to the endoscope light source unit, the endoscope light source unit including an aperture device including a plurality of aperture openings of different opening ratios which are selectively positioned between the incident end face of the light guide and the light source; a reading device for reading endoscope-type information from a memory provided in the endoscope; and a controller for selecting one aperture opening from among the aperture openings, an opening ratio of which corresponds to the endoscope-type information read by the reading device, for making the selected one aperture opening positioned between the incident end face of the light guide and the light source, and for allowing the light source to be turned ON. The controller prohibits the light source from being turned ON in the case where the reading device cannot read the endoscope-type information when the endoscope is connected to the endoscope light source unit.

It is desirable for the endoscope light source unit to include a lamp switch wherein when the lamp switch is turned ON, the controller turns ON the light source after positioning the selected one aperture opening between the incident end face of the light guide and the light source.

It is desirable for the endoscope-type information to include information on the illumination-light quantity limit, wherein the aperture openings of the different opening ratios include different aperture openings which are selectively positioned between the incident end face of the light guide and the light source by the controller in accordance with the endoscope-type information which is read by the reading device. In the case where the reading device cannot read the information on the illumination-light quantity limit when the endoscope is connected to the endoscope light source unit, the controller selects an aperture opening of a minimum opening ratio from among the different aperture openings, and prohibits the light source from being turned ON even if the lamp switch is turned ON.

It is desirable for the endoscope-type information to include information on the illumination-light quantity limit which is measured and set in advance in terms of light quantity and temperature.

It is desirable for the endoscope light source unit to include a forced light switch wherein in the case where the reading device cannot read the information on the illumination-light quantity limit when the endoscope is connected to the endoscope light source unit, the controller selects an aperture opening of a minimum opening ratio from among the different aperture openings if the forced Tight switch is turned ON, and the controller turns ON the light source.

It is desirable for the aperture device to include a disc in which the aperture openings are formed at equi-angular intervals about a center of rotation of the disc, and a drive device for rotatably driving the disc. The controller controls the drive device so that one of the aperture openings intersects an illumination optical path between the incident end face of the light guide and the light source.

It is desirable for each of the aperture openings to include a plurality of small holes formed in the disc at predetermined intervals, and for the opening ratios to be determined by differing densities of the small holes.

It is desirable for each of the aperture openings to include a plurality of small holes formed in the disc at predetermined intervals, and for the opening ratios to be determined by differing diameters of the small holes.

It is desirable for each of the aperture openings to include a plurality of small holes formed in the disc at predetermined intervals, and for the opening ratios are determined by differing densities and diameters of the small holes.

In an embodiment, an endoscope light source unit is provided, including a light source; an aperture device including a plurality of aperture openings of different opening ratios which are selectively positioned between the light source and an incident end face of a light guide of an endoscope which is disconnectably connected to the endoscope light source unit; a reading device for reading information including at least an illumination-light quantity limit of the endoscope from a memory provided in the endoscope; and a controller for making one of the aperture openings positioned between the incident end face of the light guide and the light source, and for prohibiting the light source from being turned ON in the case where the reading device cannot read the information when the endoscope is connected to the endoscope light source unit. An opening ratio of the one of the aperture openings corresponds to the information read by the reading device. According to the present invention, since the light source for an endoscope does not light up it information on the maximum amount of illumination light allowable into the scope, illumination-light quantity limit and other information of the scope connected to the endoscope light source unit is unknown, there is no possibility of an amount of illumination light which exceeds the maximum amount of illumination light allowable into a scope being supplied to the scope even if the scope whose maximum allowable amount of illumination light is small, which makes it possible to prevent overheating of the scope.

The present disclosure relates to subject matter contained in Japanese Patent Application No, 2005-330457 (filed on Nov. 15, 2005), which is expressly incorporated herein in its entirety.

BRIEF DESCRIPTION OF THE DRAWINGS

The present invention will be discussed below in detail with reference to the accompanying drawings, in which.

DESCRIPTION OF THE PREFERRED EMBODIMENT

Figure 1:
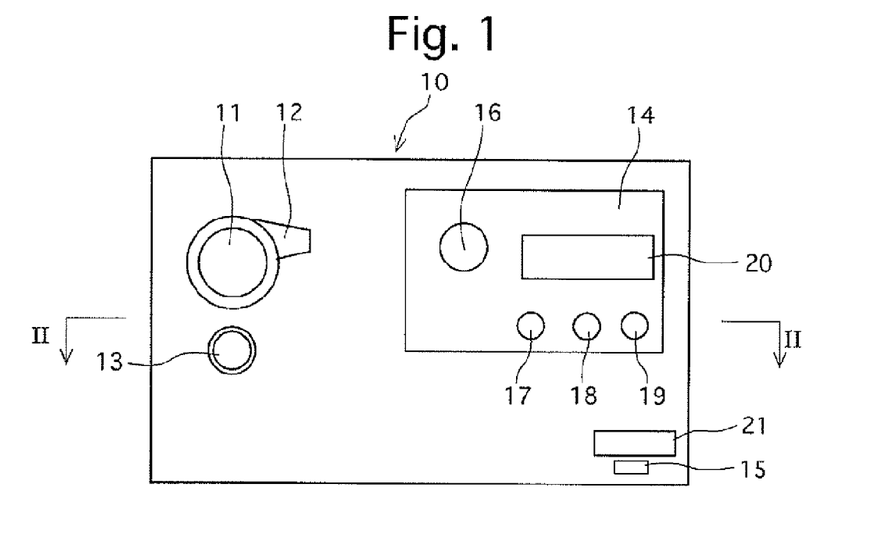
FIG. 1 is a front elevational view of an embodiment of a processor serving as an endoscope light source unit according to the present, showing an overview of the processor.
Figure 2:
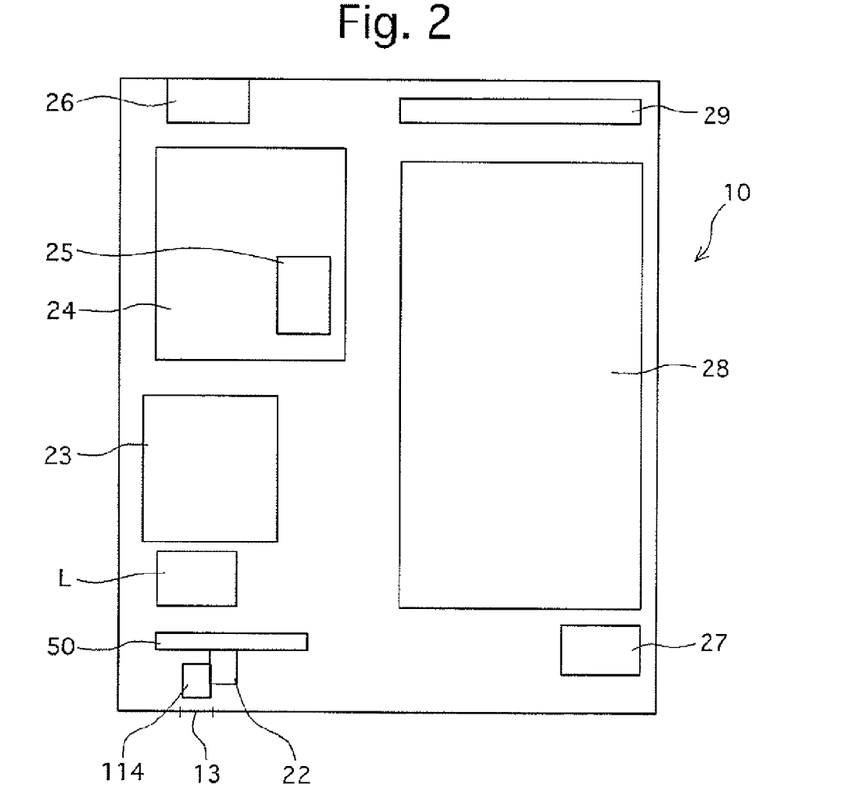
FIG. 2 is an abbreviated cross sectional view taken along the II-II line shown in FIG. 1, showing main components of the processor.

FIG. 1 is a front elevational view of a processor 10 that serves as an endoscope light source unit according to the present invention. FIG. 2 is an abbreviated cross sectional view taken along II-II line shown in FIG. 1, showing main components of the processor 10.

The processor 10 is provided on the front thereof (as viewed in FIG. 1) with a scope socket 11 into which a connector 104 of an electronic scope (electronic endoscope) 100 is to be inserted (see FIG. 4), and a scope lock lever 12 for locking the inserted connector 104 so as not to come off. The scope socket 11 establishes connection with connect pins, or the like, provided in the connector 104 of the electronic scope 100. A light guide socket 13 for the light guide connector 115 of the electronic scope 100 (or a fiber scope) to be inserted into is formed below the scope socket 11.

The processor 10 also has an operation panel 14 on the front, beside the scope socket 11. This operation panel 14 is provided with operation switches such as a lamp switch 16, an image quality adjustment switch (image quality adjustment button) 17, a light control selection switch (light control selection button) 18, a manual adjustment switch (aperture select button) 19, and a scope information display 20. A memory card slot 21 for a removable memory card to be loaded into and a main switch 15 are also formed below the operation panel 14.

The processor 10 contains a rotary aperture plate 50 which is arranged behind the light guide socket 13. This rotary aperture plate 50 has a plurality of aperture openings having different opening ratios, which are arranged in the circumferential direction of this circular plate. The rotary aperture plate 50 is driven by an aperture plate drive motor (drive device) 22 so that any one of the aperture openings is opposed to an incident end face 113a of a light guide 113 which is plugged into the light guide socket 13 (see FIG. 4). A condenser lens L is arranged on the opposite side of the rotary aperture plate 50 from the incident end face 113a, with a lamp (light source) 23 provided behind the condenser lens L. As shown in FIG. 5, the light source 23 has a built-in high-intensity lamp 35. Illumination light emitted from the lamp 35 is concentrated by the condenser lens L so that the light beam passing through any one of the aperture openings of the rotary aperture plate 50 is incident on the incident end face 113a. The end of the light guide 113 in the vicinity of the incident end face 113a is fixed inside a light guide sleeve 114 which is made of metal.

As shown in FIG. 2, the processor 10 also contains a lamp power supply 24 which has an igniter 25 for turning on the light source 23. A cooling fan 26 for cooling the lamp power supply 24 is formed on the rear panel of the processor 10.

In the processor 10, a memory card board 27 is arranged near the memory card slot 21. The memory card board 27 is electrically connected with the memory card loaded in the memory card slot 21, and functions as an interface circuit that controls reading and writing from/to the memory card. For example, the read/write control includes reading information written in the memory card, and writing information such as image information processed by the processor 10 to the memory card. The processor 10 also contains a control board 28 on which circuits such as a control circuit (controller/reading device) 41 and an image processing circuit are mounted. The control circuit 41 controls the operations of the entire processor 10, including the control of the memory card board 27 and the aperture plate drive motor 22. The image processing circuit of the control board 28 reads stored information from an EEPROM (memory) 109 of the electronic scope 100, drives a CCD sensor (image pickup device) 105 of the electronic scope 100, processes picture signals obtained by the CCD sensor 105, and displays the processed picture signals on a monitor display 43. The picture signals processed by the control board 28 are output from a picture connector (not shown) provided on a back panel substrate 29. A predetermined picture is then displayed on the monitor display 43.

Figure 3:
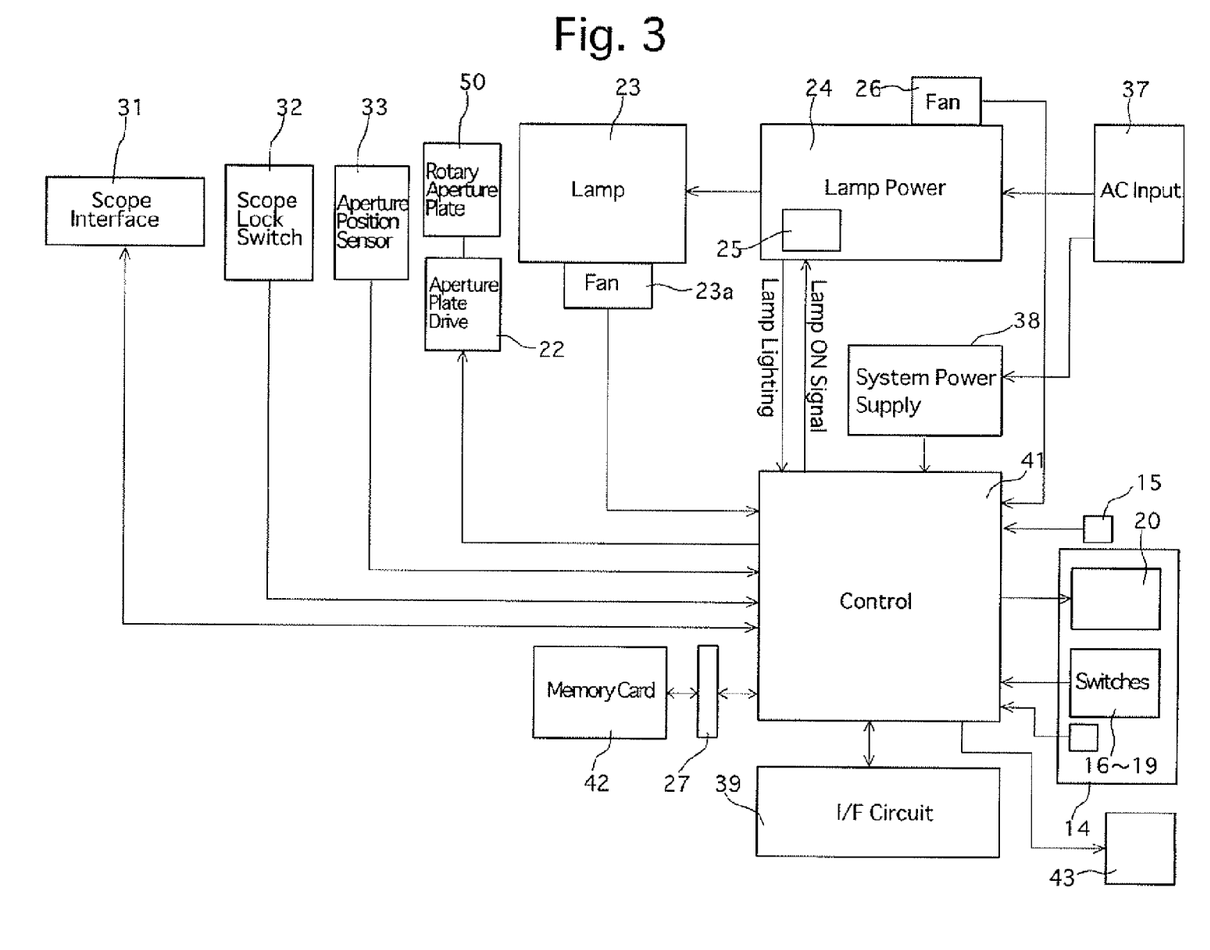
FIG. 3 is a block diagram of a main circuit of the processor.

FIG. 3 is a block diagram of main components of the circuit configuration of the processor 10. A scope interface 31 is provided inside the scope socket 11. The scope interface 31 is provided with a plurality of connectors, including an information connector and the picture connector. The information connector is for reading information written in the EEPROM 109 of the electronic scope 100. The picture connector transmits a drive clock of the CCD sensor 105, and inputs picture signals output from the CCD sensor 105. Each connector is connected to corresponding terminals, such as those of the control circuit 41 formed on the control substrate 28.

A scope lock switch 32 is a detection switch for detecting if the scope lock lever 12 is in a locked state. The state signal of the scope lock switch 32 is input to the control circuit 41.

The aperture plate drive motor 22 for rotationally driving the rotary aperture plate 50 is driven and controlled by the control circuit 41. The rotation position of the rotary aperture plate 50 is detected by an aperture position sensor 33 and the control circuit 41 receives the signal detected thereby.

The light source 23 is turned on by the igniter 25 of the lamp power supply 24 which is controlled ON/OFF by the control circuit 41. The light source 23 is also provided with a lamp cooling fan 23a. The lamp cooling fan 23a is driven and controlled by the control circuit 41. The igniter 25 for turning ON and driving the light source 23 is driven by the lamp power supply 24 which is powered by an AC input 37, typically a commercial alternating-current power.

The AC input 37 also powers a system power supply 38 which outputs a constant voltage for driving electronic circuits such as the control circuit 41. The control circuit 41 receives the constant voltage from the system power supply 38 to be activated to start processing when the main switch 15 is turned ON, and transmits a lamp-ON signal to the lamp power supply 24 to turn ON the light source 23 via the igniter 25 when the lamp switch 16 is turned ON.

The control circuit 41 reads aperture-related information from the EEPROM 109 of the electronic scope 100 via the scope interface 31, and selects a maximum opening ratio of the rotary aperture plate 50 for use when adjusting the amount of the illumination light. In this case, the scope interface 31 functions as reading device.

The control circuit 41 also performs image capturing processing for driving the CCD sensor 105 of the electronic scope 100 and inputs an image signal from the CCD sensor 105 via the scope interface 31. Thereafter, the control circuit 41 performs a predetermined image signal process, and displays the image signal on the monitor display 43 or writes the image data thereof to the memory card 42 via the card board 27. It should be appreciated that if the control circuit 41 starts the image capturing process when the main switch 15 is turned ON, the image capturing process is usually performed by an image processing circuit which is separate from the control circuit 41.

The control circuit 41 is also connected with an input device such as a keyboard via an I/F circuit 39 so that individual information necessary for endoscopic inspection can be entered via the input device.

Figure 4:
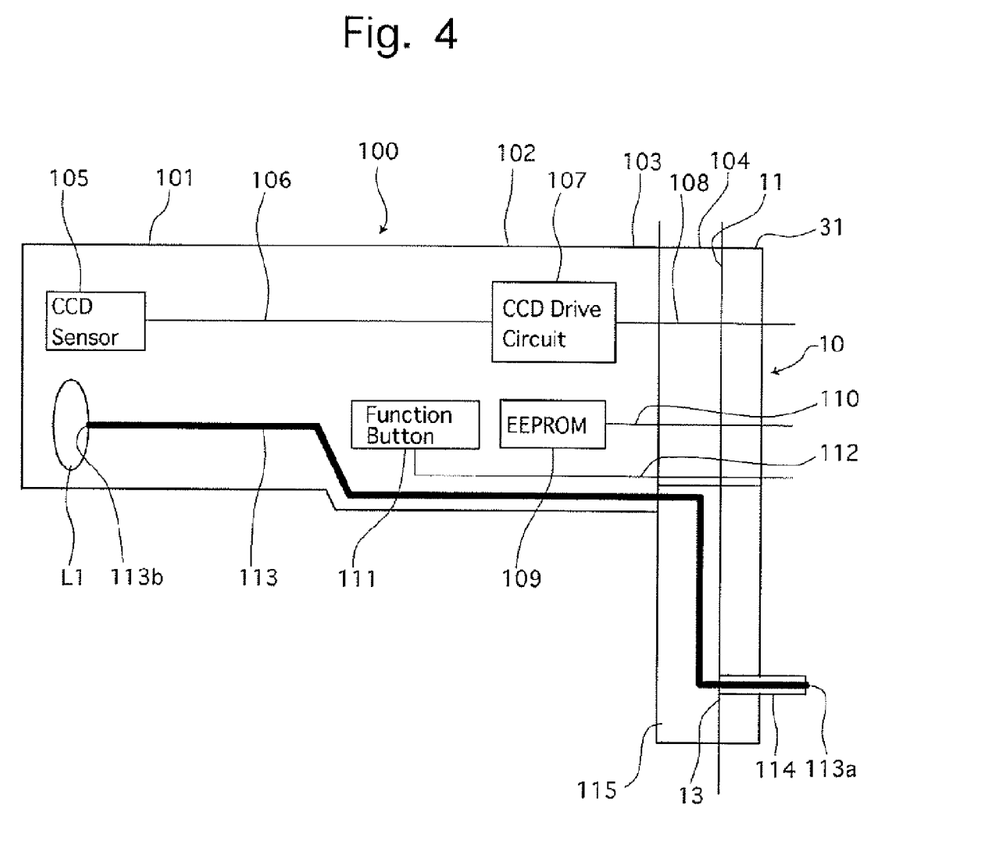
FIG. 4 is a schematic diagram of a major part of an electronic scope which is connectable to the processor.
Figure 5:
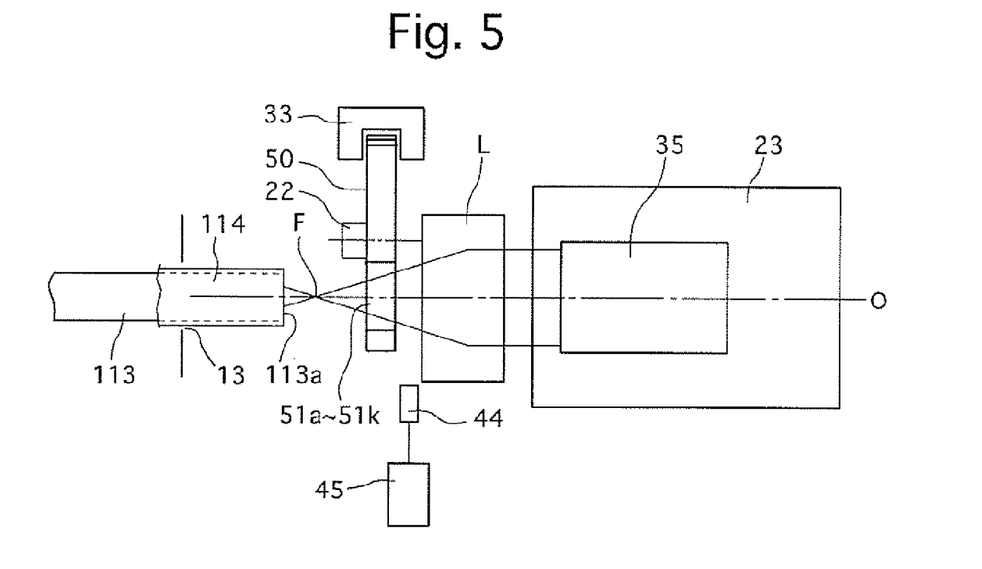
FIG. 5 is an explanatory diagram showing various components which are provided in the vicinity of the light source of the processor.

FIG. 4 is a diagram showing a schematic view of a major part of the electronic scope 100 which is connectable to the processor 10. As shown in FIG. 4, the electronic scope 100 has a flexible insertion portion 101 and an operation portion 102. The connector 104 is arranged at the proximal end of a universal tube 103 which extends from the operation portion 102. The CCD sensor 105 and a light distribution lens L1 for light illumination are arranged at the distal end of the flexible insertion portion 101. The CCD sensor 105 is connected to a CCD drive circuit 107 provided in the operation portion 102, via a picture line 106 which is laid through the insertion portion 101. The CCD drive circuit 107 is also connected with signal pins formed in the connector 104 via a picture transmission line 108 that is laid through the operation portion 102 and the universal tube 103.

The EEPROM 109, containing such information as the type of the electronic scope 100, is provided in the operation portion 102. A read/write line 110, which is connected with input and output terminals of the EEPROM 109, is connected to signal pins of the connector 104. The operation portion 102 also includes a function button 111 for making operations of taking a moving image, and photographing a still image, etc. A switch line 112 in connection with the contacts of the function button 111 is connected to signal pins in the connector 104.

The exit end 113b of the light guide 113 is placed behind the light distribution lens L1. The light guide 113 is introduced through the insertion portion 101, the operation portion 102, the universal tube 103 and the connector 104, and is inserted and fixed inside the light guide sleeve 114 which protrudes out of the connector 104. The incident end face 113a of the light guide 113 is opposed to the open end of the light guide sleeve 114.

The EEPROM 109 provided in the electronic scope 100 contains at least the information for identifying the type of scope (endoscope-type information), i.e., an illumination-light quantity limit to the scope. In this embodiment, scope types are classified into a plurality of groups stepwise depending on the illumination-light quantity limit (i.e., the maximum amounts of illumination light allowed for the light guide 113 to emit). In the present embodiment, the scope types are classified into three groups, i.e., type A, type B, and type C, in descending order of the amount of light.

FIG. 5 is a diagram showing various components which are provided in the vicinity of the light source 23 of the processor 10. As shown in FIG. 5, the condenser lens L is interposed between the incident end face 113a of the light guide sleeve 114 (light guide 113), which is inserted from the light guide socket 13, and the light source 23; and the rotary aperture plate 50 is interposed between the incident end face 113a and the condenser lens L. The incident end face 113a is normally placed orthogonal to the optical axis 0 of the condenser lens L, away from the focal point F of the condenser lens L. The substantially parallel illumination light emitted from the lamp 35 is concentrated toward the focal point F by the condenser lens L so that the light beam passing through the rotary aperture plate 50 converges at the focal point F and thereafter diverges so as to be incident on the incident end face 113a, The illumination light beam entering from the incident end face 13a is guided through the light guide 113, and emitted from the exit end 113b (see FIG. 4) of the light guide 113 provided at the distal end of the insertion portion 101. The emitted light then passes through the light distribution lens L1 for distribution (FIG. 4) so as to illuminate an object.

Figure 6:
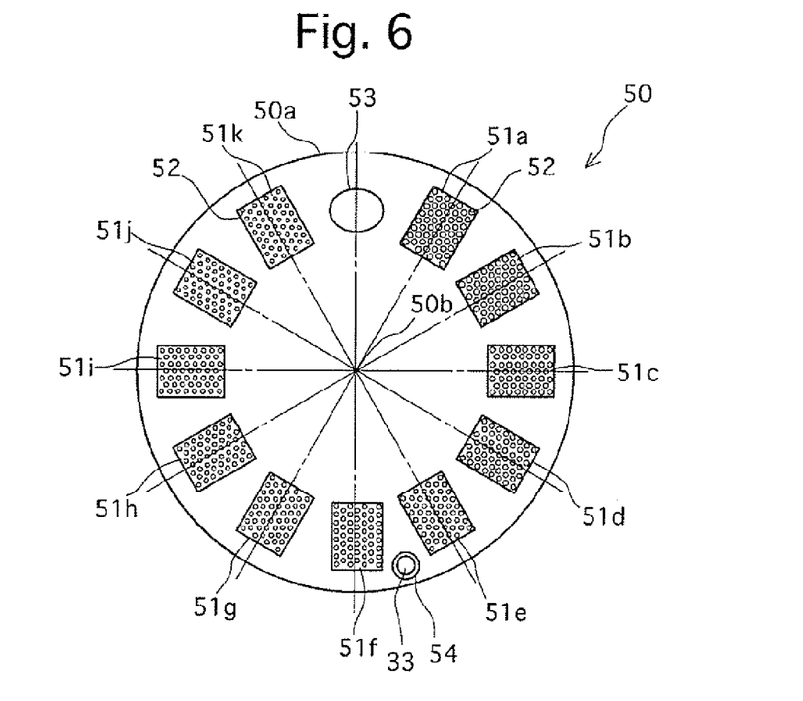
FIG. 6 is a front elevation as view of the rotary aperture plate in an embodiment of an aperture device for the light source of the processor.

FIG. 6 is a front elevational view of the rotary aperture plate 50 as an embodiment of an aperture device for the light source 23. As shown in FIG. 6, the rotary aperture plate 50 is made of an aluminum disc 50a. The disc 50a is fixed to a rotary shaft of the aperture plate drive motor 22 centered at a center of rotation 50b. The disc 50a has twelve openings which are formed at predetermined intervals circumferentially about the center of rotation 50b (at 30 degree intervals). In the illustrated embodiment, the disc 50a is provided with first to eleventh aperture openings 51a to 51k, and an auxiliary lamp opening 53. The first aperture opening 51a has an opening ratio of 75%. The opening ratios are determined to decrease stepwise, clockwise from the first aperture opening 51a. The second to eleventh aperture openings 51b to 51k have opening ratios of 50%, 35%, 25%, 18%, 13%, 9%, 7%, 5%, 3.5%, and 2%, respectively. The auxiliary lamp opening 53 has an opening ratio of 100%.

In the electronic scope 100 of the illustrated embodiment, type A corresponds to the amount of light when the aperture opening 51a having a maximum opening ratio of 75% is set, type B corresponds to the amount of light when the aperture opening 51b having a maximum opening ratio of 50% is set, and type C corresponds to the amount of light when the aperture opening 51c having a maximum opening ratio of 35% is set.

In the illustrated embodiment, the first to eleventh aperture openings 51a to 51k have a large number of small holes 52 which are formed at a predetermined spacing in each opening area. The illumination light is either passed through these small holes 52 or blocked by the surface of the disc 50a where the small holes 52 are not formed.

In an embodiment, different opening ratios are achieved by modifying the density (spacing) of the small holes 52 of first to eleventh aperture openings 51a to 51k. Alternatively, the density (spacing) can be maintained constant and the diameters of the small holes 52 of the first to eleventh aperture openings 51a to 51k can be modified. Alternatively, both the density (spacing) and the diameter of the small holes 52 of the first to eleventh aperture openings 51a to 51k can be modified. The small holes 52 can have any shape. Each the first to eleventh aperture openings 51a to 51k may be provided with a mixture of small holes of various shapes, or may have small holes of respective different shapes. Although circular small holes are easy to form and to modify in diameter, polygonal and other shapes may also be adopted. Polygonal shapes can easily provide higher opening ratios than with circular shapes.

The rotary aperture plate 50 is driven stepwise by the aperture plate drive motor 22. It is desirable for the aperture plate drive motor 22 to be a stepping motor. In the illustrated embodiment, a stepping motor having a step angle of 0.75 degrees is used. Namely, when the aperture plate drive motor 22 rotates by 40 steps, the rotary aperture plate 50 is rotated by 30 degrees, i.e., by one aperture opening.

The rotary aperture plate 50 has an aperture position hole 54 for detecting an initial position of rotation thereof. The aperture position sensor 33 (FIG. 5) is arranged so as to detect this aperture position hole 54 when the rotary aperture plate 50 is in the initial position of rotation. In the illustrated embodiment, the aperture position hole 54 is provided in between the aperture openings 51e and 51f. Accordingly the initial position of the rotary aperture plate 50 is determined at a rotational position such that the aperture opening 51c is positioned in the illumination optical path; the aperture opening 51c having a maximum opening ratio of 35% which is deemed as being a safe opening ratio, i.e., an opening ratio which prevents an excessively large quantity of the illumination light from passing therethrough, for any electronic scope which can be mounted to the processor 10. The aperture position sensor 33 can be a photo coupler, wherein the aperture position hole 54 opens the optical path of the photo coupler when the rotary aperture plate 50 is in the initial position; the disc 50a otherwise blocks the optical path of the photo coupler. In the present embodiment, the initial position refers to the state where the third aperture opening 51c that has a maximum opening ratio of 35% enters (intersects) the illumination optical path.

Note that the initial position of the rotary aperture plate 50 can be alternatively be determined at a rotational position such that one of the aperture openings 51d through 51k, which have a lower opening ratio than the aperture opening 51c, is positioned in the illumination optical path. Accordingly, the rotary aperture plate 50 is rotated from the initial position at one of the aperture openings 51d through 51k until the aperture opening 51c is positioned in the illumination optical path.

As shown in FIG. 5, the processor 10 has an auxiliary light 44 that comes into operation when the lamp 35 of the light source 23 goes out due to some reason (e.g. due to the expiration of the lifetime). when the control circuit 41 detects that the lamp 35 has gone out, the control circuit 41 activates an auxiliary light drive mechanism 45 to put the auxiliary light 44 into the illumination optical path and turn the auxiliary light ON. The control circuit 41 rotates the rotary aperture plate 50 so that the auxiliary lamp opening 53 enters (intersects) the illumination optical path.

Figure 7:
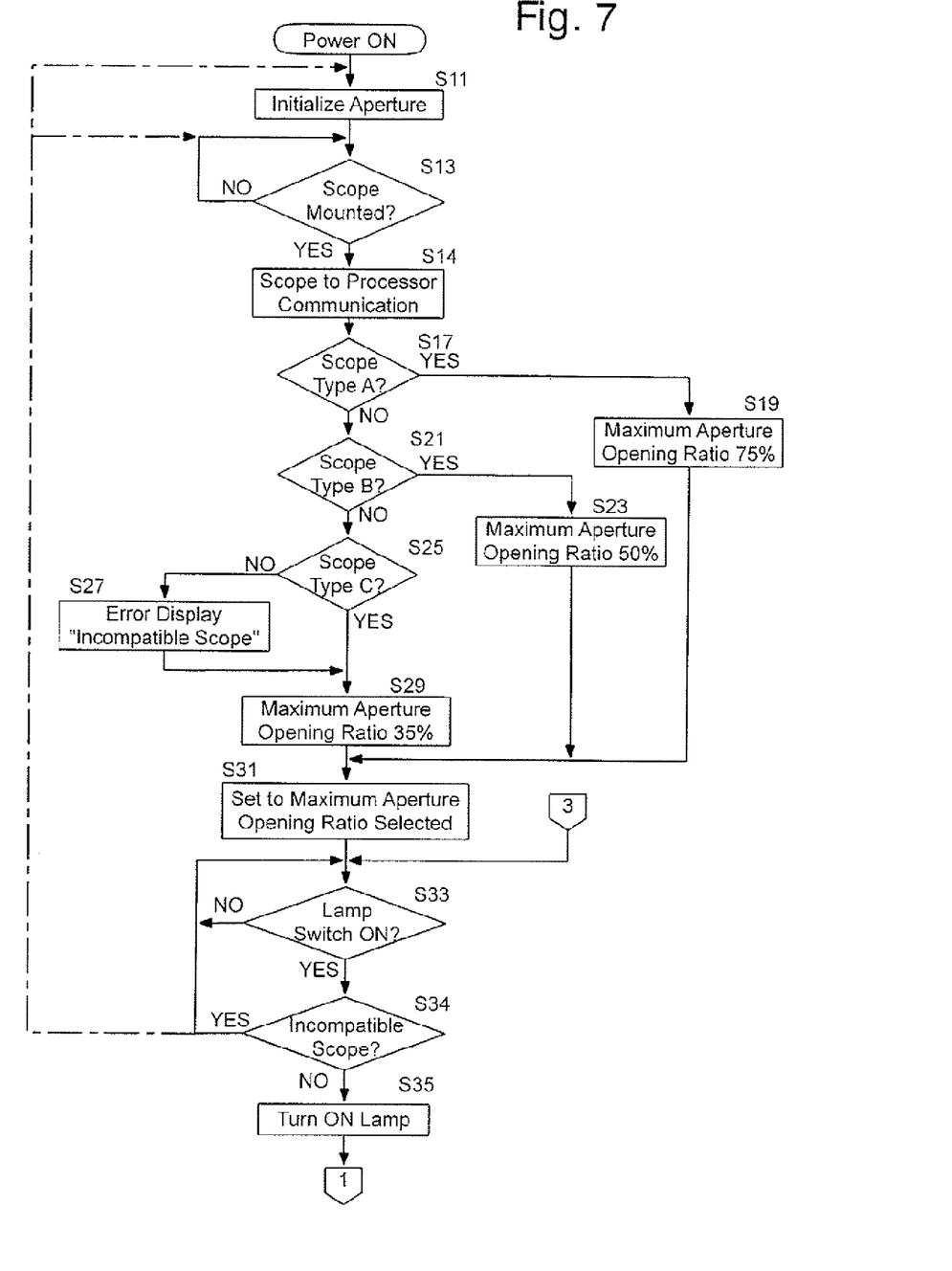
FIG. 7 is a flowchart showing an embodiment of a first half of a control operation for illumination of the processor.
Figure 8:
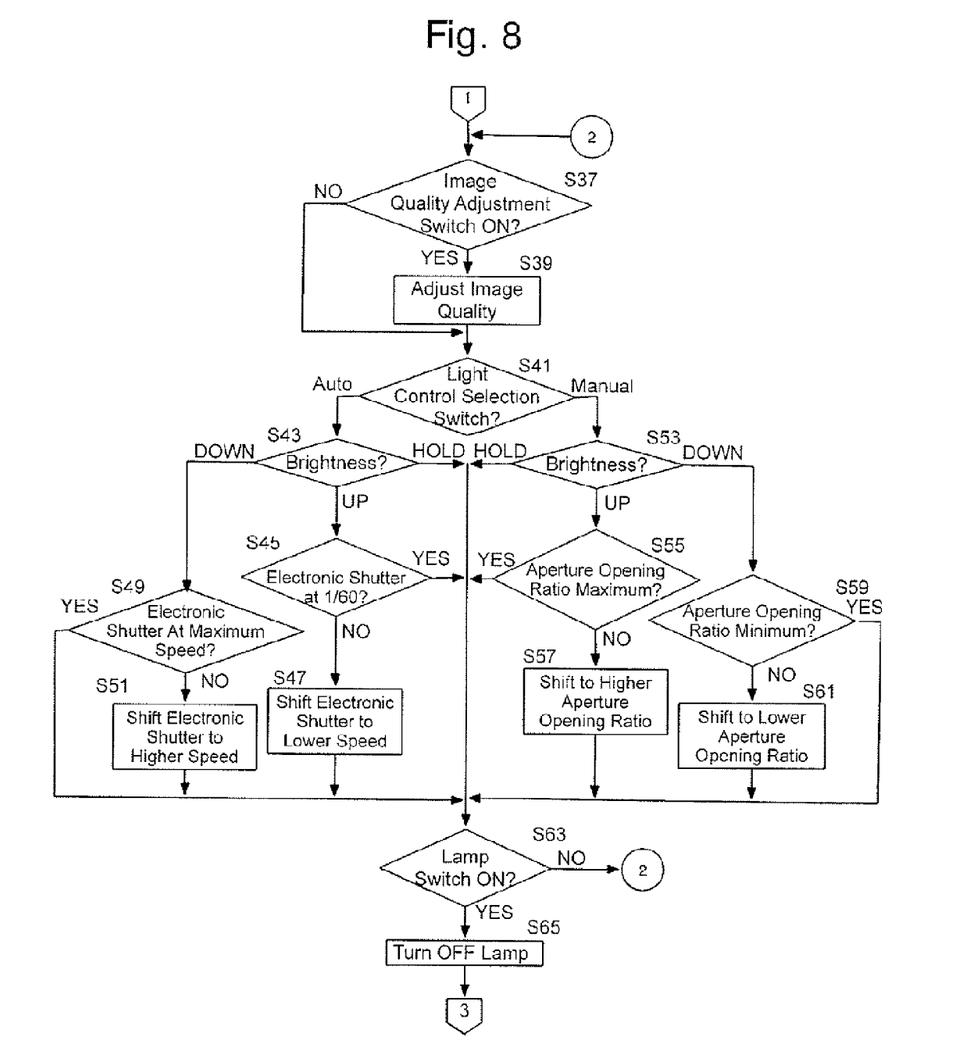
FIG. 8 is a flowchart showing a second half of the control operation shown in FIG. 7.

The operation of the electronic endoscope system will be hereinafter described with reference to the flowchart of the power-ON process shown in FIGS. 7 and 8. The power-ON process concerns the operation of the control circuit 41. The control circuit 41 enters this power-ON process when the main switch 15 is turned ON.

Upon entering the power-ON process, the control circuit 41 first initializes the state of the rotary aperture plate 50 (step S11). In the present embodiment, the initialization refers to rotating the rotary aperture plate 50 so that the third aperture opening 51c having an opening ratio of 35% enters into (intersects) the illumination optical path.

Thereafter, the control circuit 41 checks if an scope is mounted (step S13). In this embodiment, it is determined a scope is mounted if the scope lock switch 32 is ON. If a scope is mounted (step S13, YES), the mounted scope and the processor perform scope-to-processor communication so as to input scope information (step S14). The scope information includes at least information concerning the amount of illumination light, i.e., one of scope types A to C in the illustrated embodiment.

Based on the input scope information, the control circuit 41 checks whether the scope is a scope type A (step S17), scope type B (step S21), or scope type C (step S25). In the case of a scope type A (S17, YES), the control circuit 41 selects a maximum aperture opening ratio of 75% (step S19). In the case of a scope type B (step S17, NO; step 821, YES), the control circuit 41 selects a maximum aperture opening ratio of 50% (step S23). In the case of a scope type C (step S17, NO; step S21, NO; step S25, YES), the control circuit 41 selects a maximum aperture opening ratio of 35% (step S29). If the mounted scope is none of scope types A, B, and C (step S17, NO; step S21, NO; step S25, NO), the control circuit 41 displays "incompatible scope" on the scope information display unit 20 or the monitor display 43 (step S27), and selects a maximum opening ratio of 35% (step S29). The maximum opening ratio selected here is used as the upper limit of the opening ratios in automatic light control processing and manual light control processing so that opening ratios higher than the selected one will not be set. This regulation precludes heat generation caused by excessive illumination light.

The control circuit 41 rotates the rotary aperture plate 50 stepwise so that one of the first to eleventh aperture openings 51a to 51k corresponding to the maximum aperture opening ratio selected at step S19, S23, or S29 is set (step S31). After one of the first to eleventh aperture openings 51a to 51k corresponding to the maximum aperture opening ratio selected is set, the control circuit 41 checks whether or not the lamp switch 16 is operated when the lamp 35 is OFF (step S33). The control circuit 41 repeats checking while the lamp switch 16 is not operated (step S33, NO; step S33). It should be noted that the lamp switch 16 according to the illustrated embodiment is a momentary switch. The control circuit 41 turns ON the lamp 35 if the lamp switch 16 is operated when the lamp 35 is OFF, and turns OFF the lamp 35 if the lamp switch 16 is operated while the lamp 35 is ON.

When the lamp switch 16 is operated (step S33, YES), the control circuit 41 checks whether or not the mounted scope is an incompatible scope (step S34) If the mounted scope is an incompatible scope (step S34, YES), the control circuit 41 returns to step S33 so as not to turn ON the lamp 35. The control circuit 41 returns to step S11 if the main switch 15 is turned ON in the OFF state or if the mounted scope is detached while the control circuit 41 repeats the operations at steps S33 and S34. In an alternative embodiment, if the mounted scope is an incompatible scope (step S34, YES), control can return to either step S11 or S13.

If the mounted scope is not an incompatible scope (step S34, NO), i.e., if the mounted scope is one of scope types A to C, the control circuit 41 turns ON the lamp 35 (step S35). Thereafter, the control circuit 41 checks whether or not the image quality adjustment switch 17 is ON (step S37). If the image quality adjustment switch 17 is ON, the control circuit 41 carries out an image quality adjustment and proceeds to step S41 (step S37, YES; step S39; and step S41). If the image adjustment switch is not ON, the control circuit 41 skips the image quality adjustment and proceeds to step S41 (step S37, NO; step S41).

At step S41, the control circuit 41 checks whether automatic light control or manual light control has been selected by the light control selection switch 18.

If the automatic light control is selected (step S41, AUTO), the control circuit 41 checks whether to increase, decrease, or hold the brightness based on the brightness of the object image measured by the control circuit 41 (step S43). In order to increase the brightness (step S43 UP), i.e., adjust toward an overexposure, the control circuit 41 checks whether or not the electronic shutter is set to a minimum speed of 1/60 second (step S45). If the shutter speed is already set to 1/60 second, the control circuit 41 simply proceeds to step S63 since it is impossible to slow down the shutter speed further (step S45; YES, S63). If the shutter speed is not set to 1/60 second (step S45, NO), the control circuit 41 shifts the electronic shutter to a slower speed (step S47), and proceeds to step S63.

In order to decrease the brightness (step S43, DOWN), i.e., adjust toward an underexposure, the control circuit 41 checks whether or not the electronic shutter is set to a maximum speed (step S49). If the electronic shutter is set to the maximum speed (step S49. YES), the control circuit 41 simply proceeds to step S63. If the electronic shutter is not set to the maximum speed (step S49, NO), the control circuit 41 shifts the electronic shutter to a higher speed (step S51), and proceeds to step S63.

To hold the brightness (step S43; HOLD), i.e., make no adjustment on the exposure, the control circuit 41 simply proceeds to step S63.

If the manual light control is selected (step S41, MANUAL), the control circuit 41 checks whether brightness UP, DOWN, or HOLD has been selected by the manual adjustment switch 19 (step S53). it should be noted that when the manual light control is selected in the illustrated embodiment, the electronic shutter speed is fixed to 1/60 second.

If brightness UP is selected by the manual adjustment switch 19 (step S53, UP), the control circuit 41 checks whether or not the aperture opening ratio is set to a maximum value. If the aperture opening ratio is set to the maximum value (step S55, YES), the control circuit 41 simply proceeds to step S63. If the aperture opening ratio is not set to the maximum value (step S55, NO), the control circuit 41 shifts (rotates) the rotary aperture plate 50 to a higher aperture opening ratio, up to the next level (step S57), and proceeds to step S63.

If brightness DOWN is selected by the manual adjustment switch 19 (step S53, DOWN), the control circuit 41 checks whether or not the aperture opening ratio is set to a minimum value (step S59). If the aperture opening ratio is set to the minimum value (step S59, YES), the control circuit 41 simply proceeds to step S63. If the aperture opening ratio is not set to the minimum value (step S59, NO), the control circuit 41 shifts the aperture opening ratio, namely, rotates the rotary aperture plate 50 down to the next level (step S61), and proceeds to step S63.

If no selection is made by the manual adjustment switch 19 (step S53, HOLD), the control circuit 41 simply proceeds to step S63.

At step S63, the control circuit 41 checks whether or not the lamp switch 16 is operated while the lamp 35 is ON. If the lamp switch 16 is not operated (step S63, NO), the control circuit 41 returns to step S37. If the lamp switch 16 is operated (step S63, YES), the control circuit 41 turns OFF the lamp 35 (step S65), and returns to step S33.

When the main switch 15 is turned OFF, the control circuit 41 turns OFF the lamp 35 and exits the power-ON process via an interrupt process.

As described above, according to the present invention, the lamp 35 is not turned ON if an incompatible scope which cannot utilize the light quantity limiting capability of the processor 10 (e.g., an electronic scope having no information on an illumination-light quantity limit of the processor 10) is mounted to the processor 10, so that problems such as overheating of a scope can be prevented from occurring. On the other hand, if a scope compatible with the processor 10 is connected to the processor 10, the amount of illumination light is regulated depending on the type of scope connected to the processor 10. Consequently, even if the amount of light of the scope connected is high, it is possible to prevent the scope end from rising in temperature excessively due to an excessive amount of light. Even if the maximum amount of light allowable into the scope connected is low, it is possible to obtain a sufficient amount of light.

Although the aperture device for the light source 23 is set to the maximum aperture opening ratio of 35% and does not turn ON the lamp 35 even if the lamp switch 16 is ON if it is determined that the mounted scope is none of scope types A, B, and C or an incompatible scope in the above described embodiment, the processor 10 can be further provided with a forced light switch 16a so that the lamp 35 is turned ON by an operation of this forced light switch 16a. This is because there are cases where it is obvious that the maximum amount of light is sufficiently great even if the mounted scope is incompatible with the processor 10.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. An endoscope light source unit including a light source, for making illumination light from said light source incident on an incident end face of a light guide of an endoscope which is disconnectably connected to said endoscope light source unit, said endoscope light source unit comprising:

- an aperture device including a plurality of aperture openings of different opening ratios which are selectively positioned between said incident end face of said light guide and said light source;
- a reading device for reading endoscope-type information from a memory provided in said endoscope; and
- a controller for selecting one aperture opening from among said aperture openings, an opening ratio of which corresponds to said endoscope-type information read by said reading device, for making said selected one aperture opening positioned between said incident end face of said light guide and said light source, and for allowing said light source to be turned ON,
- wherein said controller prohibits said light source from being turned ON in the case where said reading device cannot read said endoscope-type information when said endoscope is connected to said endoscope light source unit.

2. The endoscope light source unit according to claim 1, further comprising a lamp switch wherein when said lamp switch is turned ON, said controller turns ON said light source after positioning said selected one aperture opening between said incident end face of said light guide and said light source.

3. The endoscope light source unit according to claim 2, wherein said endoscope-type information comprises information on said illumination-light quantity limit,
- wherein said aperture openings of said different opening ratios include different aperture openings which are selectively positioned between said incident end face of said light guide and said light source by said controller in accordance with said endoscope-type information which is read by said reading device, and
- wherein, in the case where said reading device cannot read said information on said illumination-light quantity limit when said endoscope is connected to said endoscope light source unit, said controller selects an aperture opening of a minimum opening ratio from among said different aperture openings, and prohibits said light source from being turned ON even if said lamp switch is turned ON.

4. The endoscope light source unit according to claim 1, wherein said endoscope-type information comprises information on said illumination-light quantity limit which is measured and set in advance in terms of light quantity and temperature.

5. The endoscope light source unit according to claim 1, further comprising a forced light switch wherein in the case where said reading device cannot read said information on said illumination-light quantity limit when said endoscope is connected to said endoscope light source unit, said controller selects an aperture opening of a minimum opening ratio from among said different aperture openings if said forced light switch is turned ON, and said controller turns ON said light source.

6. The endoscope light source unit according to claim 1, wherein said aperture device comprises:
- a disc in which said aperture openings are formed at equiangular intervals about a center of rotation of said disc; and
- a drive device for rotatably driving said disc,
- wherein said controller controls said drive device so that one of said aperture openings intersects an illumination optical path between said incident end face of said light guide and said light source.

7. The endoscope light source unit according to claim 6, wherein each of said aperture openings comprises a plurality of small holes formed in said disc at predetermined intervals; and
- wherein said opening ratios are determined by differing densities of said small holes.

8. The endoscope light source unit according to claim 6, wherein each of said aperture openings comprises a plurality of small holes formed in said disc at predetermined intervals; and
- wherein said opening ratios are determined by differing diameters of said small holes.

9. The endoscope light source unit according to claim 6, wherein each of said aperture openings comprises a plurality of small holes formed in said disc at predetermined intervals; and
- wherein said opening ratios are determined by differing densities and diameters of said small holes.

10. An endoscope light source unit comprising:
- a light source;
- an aperture device including a plurality of aperture openings of different opening ratios which are selectively positioned between said light source and an incident end face of a light guide of an endoscope which is disconnectably connected to said endoscope light source unit;
- a reading device for reading information including at least an illumination-light quantity limit of said endoscope from a memory provided in said endoscope; and
- a controller for making one of said aperture openings positioned between said incident end face of said light guide and said light source, and for prohibiting said light source from being turned ON in the case where said reading device cannot read said information when said endoscope is connected to said endoscope light source unit,
- wherein an opening ratio of said one of said aperture openings corresponds to said information read by said reading device.

* * * * *